(12) United States Patent　　(10) Patent No.: US 12,582,290 B2
Polejaev　　(45) Date of Patent: Mar. 24, 2026

(54) TECHNIQUES FOR COMPOSITION IDENTIFICATION OF AN ANATOMICAL TARGET

(71) Applicant: GYRUS ACMI, INC., Westborough, MA (US)

(72) Inventor: Vladimir Polejaev, Middletown, CT (US)

(73) Assignee: Gyrus ACMI, Inc., Westborough, MA (US)

( * ) Notice: Subject to any disclaimer, the term of this patent is extended or adjusted under 35 U.S.C. 154(b) by 422 days.

(21) Appl. No.: 17/655,600

(22) Filed: Mar. 21, 2022

(65) Prior Publication Data

US 2022/0313062 A1　　Oct. 6, 2022

Related U.S. Application Data

(60) Provisional application No. 63/200,887, filed on Apr. 1, 2021.

(51) Int. Cl.
　*A61B 1/00*　　(2006.01)
　*A61B 1/06*　　(2006.01)
　*G01J 3/28*　　(2006.01)
(52) U.S. Cl.
　CPC ........ *A61B 1/00057* (2013.01); *A61B 1/0638* (2013.01); *G01J 3/2823* (2013.01); *G01J 2003/2866* (2013.01)
(58) Field of Classification Search
　CPC . A61B 1/00057; A61B 1/0638; A61B 5/0075; G01J 2003/2866; G01J 3/10; G01J 3/28; G01J 3/2803; G01J 3/2823
　See application file for complete search history.

(56) References Cited

U.S. PATENT DOCUMENTS 9,470,579 B2　10/2016　Ritter et al.
11,375,894 B2 *　7/2022　Lapointe .............. A61B 5/1455
(Continued)

FOREIGN PATENT DOCUMENTS

BR　112020019367　　2/2021
CN　102377947 B　*　11/2013
(Continued)

OTHER PUBLICATIONS

"Indian Application Serial No. 202244015584, First Examination Report mailed Oct. 28, 2022", 5 pgs.
(Continued)

*Primary Examiner* — Tri T Ton
(74) *Attorney, Agent, or Firm* — Schwegman Lundberg & Woessner, P.A.

(57)　　　　　ABSTRACT

Techniques for calibrating an optical sensor system of a composition identification system are provided. In an example, a method can include receiving light at an optical sensor of the optical sensor system from a reference target, determining a first spectral response of the light across a range of wavelengths, determining whether a first spectral intensity corresponding to a first wavelength of the spectral response violates a first threshold, adjust an exposure duration or gain of the optical sensor for the first wavelength to correct the violation, and repeat for multiple wavelengths in the range. Once calibrated, the optical system can more efficiently identify composition of targets, such as anatomical targets encountered during medical procedures such as during endoscopy, laparoscopy, or ureteroscopy procedures, especially when such targets are illuminated with a wide spectrum illumination source.

18 Claims, 4 Drawing Sheets

(56) References Cited

U.S. PATENT DOCUMENTS

| | | | | |
|---|---|---|---|---|
| 11,406,447 B2 * | 8/2022 | Bukesov | ............. | A61B 5/6852 |
| 2003/0007672 A1 | 1/2003 | Harman et al. | | |
| 2004/0085542 A1 * | 5/2004 | Soliz | .................... | G01J 3/2823 |
| | | | | 356/456 |
| 2007/0187027 A1 * | 8/2007 | Tausch | ............... | B41F 23/0409 |
| | | | | 156/359 |
| 2011/0149057 A1 | 6/2011 | Beck et al. | | |
| 2021/0038300 A1 * | 2/2021 | Bukesov | ............ | A61B 1/00165 |

FOREIGN PATENT DOCUMENTS

| | | | | | |
|---|---|---|---|---|---|
| CN | 113572968 A | * | 10/2021 | ............. | H04N 23/73 |
| DE | 102009058662 | | 6/2011 | | |
| DE | 102022106599 | | 10/2022 | | |
| EP | 2840368 A1 | * | 2/2015 | ........... | G01J 3/0208 |
| JP | 2005006768 | | 1/2005 | | |
| JP | 2005131129 | | 5/2005 | | |
| JP | 2014233533 A | * | 12/2014 | ........... | H04N 23/555 |
| JP | 2016510235 | | 4/2016 | | |
| JP | 2020192007 | | 12/2020 | | |
| JP | 2022159109 | | 10/2022 | | |
| JP | 7562592 | | 9/2024 | | |
| WO | 2021026145 | | 2/2021 | | |

OTHER PUBLICATIONS

"Japanese Application Serial No. 202010101270.7, Notification of Reasons for Refusal mailed Mar. 14, 2023", w English Translation, 10 pgs.

"Japanese Application Serial No. 2022-052677, Decision of Rejection mailed Sep. 12, 2023", w English Translation, 11 pgs.

"Japanese Application Serial No. 2022-052677, Notification of Reasons for Rejection mailed Feb. 14, 2024", W English Translation, 5 pgs.

"Japanese Application Serial No. 202010101270.7, Response filed Jul. 27, 2023 to Notification of Reasons for Refusal mailed Mar. 14, 2023", w english claims, 24 pgs.

"Japanese Application Serial No. 2022-052677, Response filed May 7, 2024 to Notification of Reasons for Rejection mailed Feb. 14, 2024", w english claims, 9 pgs.

"Japanese Application Serial No. 2022-052677, Response filed Dec. 21, 2023 to Decision of Rejection mailed Sep. 12, 2023", with machine translation, 21 pgs.

"German Application Serial No. 102022106599.5, Office Action mailed Jul. 29, 2025", w English translation, 12 pgs.

* cited by examiner

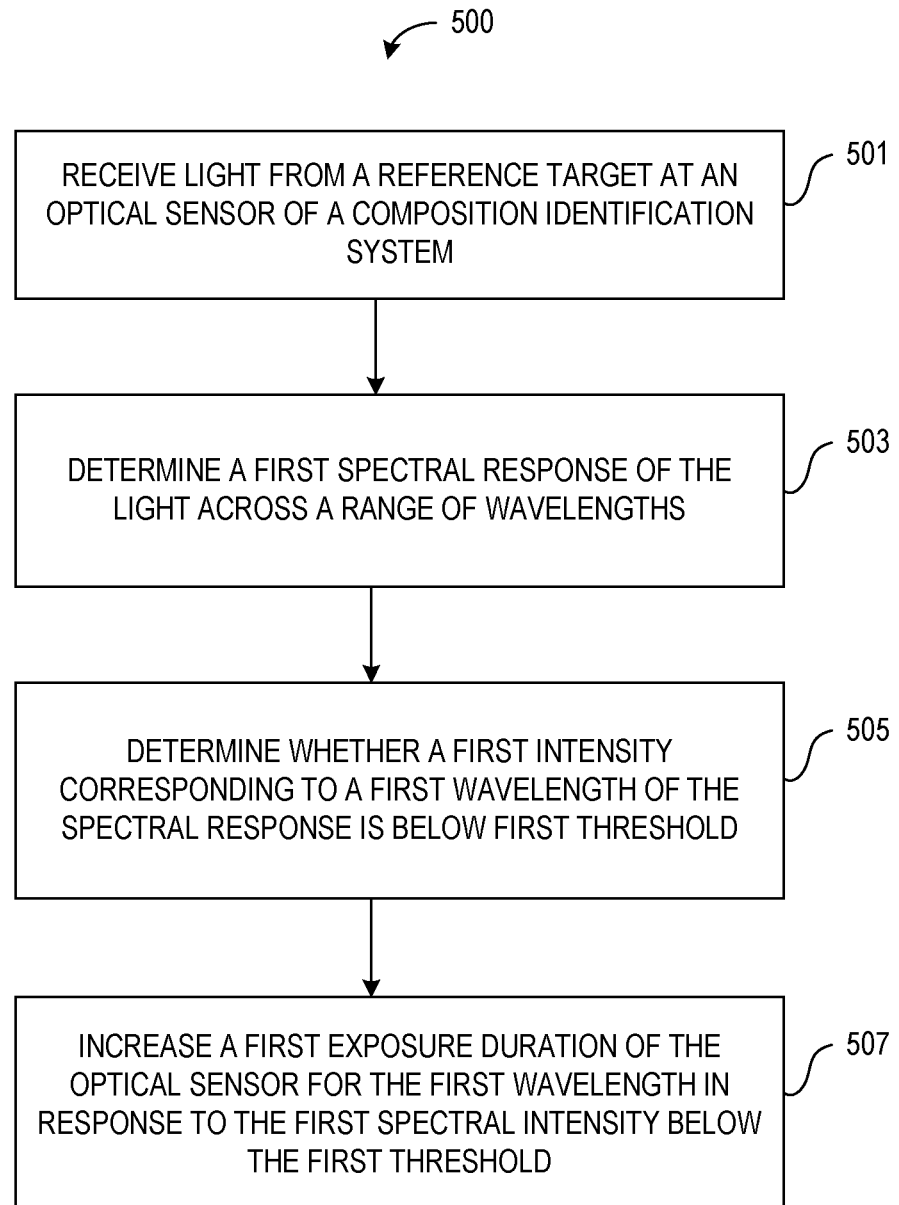

500

RECEIVE LIGHT FROM A REFERENCE TARGET AT AN OPTICAL SENSOR OF A COMPOSITION IDENTIFICATION SYSTEM — 501

DETERMINE A FIRST SPECTRAL RESPONSE OF THE LIGHT ACROSS A RANGE OF WAVELENGTHS — 503

DETERMINE WHETHER A FIRST INTENSITY CORRESPONDING TO A FIRST WAVELENGTH OF THE SPECTRAL RESPONSE IS BELOW FIRST THRESHOLD — 505

INCREASE A FIRST EXPOSURE DURATION OF THE OPTICAL SENSOR FOR THE FIRST WAVELENGTH IN RESPONSE TO THE FIRST SPECTRAL INTENSITY BELOW THE FIRST THRESHOLD — 507

*FIG. 5*

TECHNIQUES FOR COMPOSITION IDENTIFICATION OF AN ANATOMICAL TARGET

CROSS-REFERENCE TO RELATED APPLICATION

This application claims the benefit of priority to U.S. Provisional Patent Application Ser. No. 63/200,887, filed Apr. 1, 2021, the contents of which are incorporated herein by reference in their entirety.

FIELD OF THE DISCLOSURE

The present invention relates to target identification and, more particularly, to techniques for optimizing an optical composition detection system.

BACKGROUND OF THE DISCLOSURE

Medical scopes allow a user to inspect hidden areas of a patient. Scopes for visual inspection of certain internal areas of a patient, such as endoscopes and laparoscopes, were first developed in the early 1800s and have been used to inspect inside the body. A typical medical scope consists of a distal end comprising an optical or electronic imaging system and a proximal end with controls for manipulating the tools and devices for viewing the image, with a solid or tubular elongate shaft connecting the ends. Some medical scopes allow a physician to pass tools or treatments down a hollow channel, for example, to resect tissue or retrieve objects.

SUMMARY OF THE DISCLOSURE

Techniques for calibrating an optical sensor system of a composition identification system are provided. In an example, a method can include receiving light at an optical sensor of the optical sensor system from a reference target, determining a first spectral response of the light across a range of wavelengths, determining whether a first spectral intensity corresponding to a first wavelength of the spectral response violates a first threshold, adjust an exposure duration or gain of the optical sensor for the first wavelength to correct the violation, and repeat for multiple wavelengths in the range. Once calibrated, the optical system can more efficiently identify composition of targets, such as anatomical targets encountered during medical procedures such as during endoscopy, laparoscopy, or ureteroscopy procedures, especially when such targets are illuminated with a wide spectrum illumination source.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

FIG. 5 illustrates generally an example method for calibrating a composition identification system according to the present subject matter.

DETAILED DESCRIPTION

Figure 1:
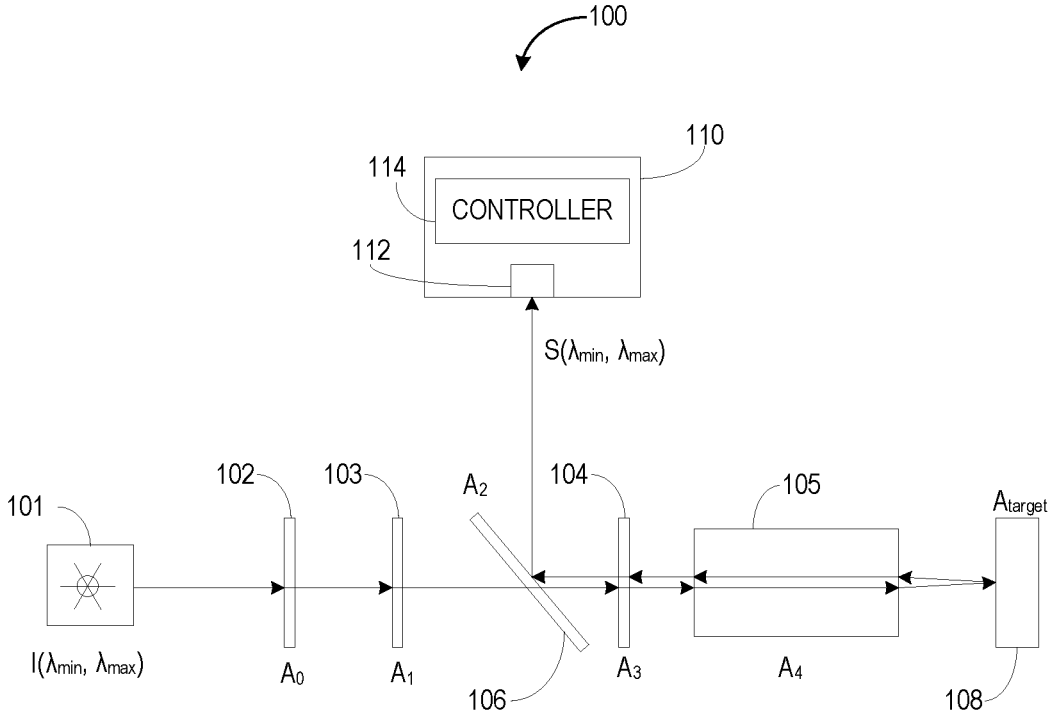
FIG. 1 illustrates generally an example composition identification system according to the present subject matter.

An image system can allow visual confirmation of an anatomical target. More sophisticated image systems can allow for detecting a spectral response of illumination light reflected from the anatomical target. Such spectral information can be used to identify the composition of the anatomical target, which can assist in efficacy of certain procedures. However, an image or optical system capable of timely, automatic composition identification can require extensive libraries of reference information because the effects of the illumination light, the optics, and the imaging or optical sensor can each affect the resulting spectral information.

A medical scope can provide a view of an anatomical target of a patient. Such medical scopes can include but are not limited to, an endoscope, laparoscope, or variations, and other types of scopes used for diagnostic and therapeutic procedures. During a medical scope procedure, a physician can control the position of the end of the scope to view an anatomical target. Whether diagnostic or therapeutic, composition of the anatomical target can provide additional information that can benefit efficiency and efficacy of many procedures. Spectral analysis is one method of detecting composition of an anatomical target. Such a method can include illuminating the target with light and capturing light reflected by the target with an optical sensor. The optical sensor can provide spectral information of the reflected light and, in turn, provide spectral information about the target, such as what wavelengths of the reflected light are affected by the composition of the target. In general, the efficiency and accuracy of the determination of the composition can be improved with a wider spectrum of illumination light.

The accuracy of identifying the composition of the target from the spectral information derived from the reflected light can depend on a number of factors including, but not limited to, the spectrum breadth and intensity of the light illuminating the target, the optics guiding light to and from the target, and the configuration of the optical sensor. Therefore, conventional systems that attempt to automatically identify composition of a target can require a massive library of reference information because each component of the system (e.g., illumination source, optics, optical sensor) can affect the interpretation of the spectral information generated by the system for any one target. The present subject matter provides techniques for using a wide-spectrum illumination source and optics to provide wide spectrum spectral information about composition of an anatomical target. The techniques adjust the operating conditions of an optical sensor system to normalize the spectrum of the illumination source and the effects of the optics based on a reference target. As such, upon receiving illumination reflected from a procedure target, the spectral differences between the normalized spectrum and the spectral information derived from the reflected illumination of the procedure target provide wide spectrum information about the composition of the procedure target. Consequently, the techniques can allow for normalizing the spectral effects of many components, and the combination of those components, such that a smaller reference library of spectral information can be used to timely, and accurately identify composition of a target during a procedure, such as a endoscopic or laparoscopic ablation procedure.

FIG. 1 illustrates generally an example composition identification system 100 according to the present subject matter. The composition identification system 100 can include an illumination source 101, optics 102, 103, 104, 105, 106 and an optical sensor system 110. In certain examples, the illumination source 101 can include multiple illumination sources and a controller. In some examples, the illumination source 101 can provide light having a wide range of wavelengths ($I(\lambda_{min}, \lambda_{max})$). In some examples, the wide range of wavelengths can span the visible light spectrum (e.g., about 400 nanometer (nm) wavelength to about 700 nm wavelength). In some examples, the range of wavelengths of the light from the illumination source 101 can also include infrared wavelengths or ultraviolet wavelengths in addition to a range of visible wavelengths. The wide spectrum of light from the illumination source 101 can provide more spectral information about the composition of a target 108 than a few beams of narrow spectrum light emitted, for example, from laser illumination sources or other narrow wavelength illumination sources.

The optics 102, 103, 104, 105, 106 can guide the light of the illumination source 101 to the target 108 as well as guide and separate light reflected from the target 108 to the optical sensor system 110. In certain examples, the optics can include one or more lenses 102, 103, 104 including focusing lenses, and collation lenses. The optics can also include mirrors, beam splitters 106, optical fibers, optical cables, etc. In some examples, the optics can include optical paths of a medical scope 105 such as the optical paths of an endoscope or laparoscope. One or more of the components of the optics can affect the spectrum of the light conducted or guided by the optical component. The spectral effects of each optical component can be represented as a function ($A_i(\lambda)$) of wavelength where "i" identifies the optical component. Such spectral effects usually represent attenuation of a given wavelength but the present subject matter is not so limited. In certain examples, the present techniques can assist in compensating spectral effects of either the illumination light 101 or the optics 102-106.

The optical sensor system 110 can include an optical sensor 112 and a controller 114. The optical sensor 112 can receive the light reflected from the target. The optical sensor can include an array of light sensitive elements that may be referred to as pixels or that define a pixel within the field of view of the optical sensor. The controller 114 can control the gain (k) and exposure duration ($\tau_{exp}$) of elements of the optical sensor 112, can receive signals from the optical sensor 112, and can provide spectral information of the reflected light for analysis of the composition of the target 108. The controller can take many different forms, such as, but not limited to, being part of the optical sensor, being separate from the optical sensor, existing on a network, existing as a cloud computing resource, or combinations thereof. For calibration, the target can be a white standard such that the signal (S) received at the optical sensor can be represented as:

$$S(\lambda_{min}, \lambda_{max}) = \prod_{i=0}^{4} A_i * A_{target} * I(\lambda_{min}, \lambda_{max})$$

Figure 2:
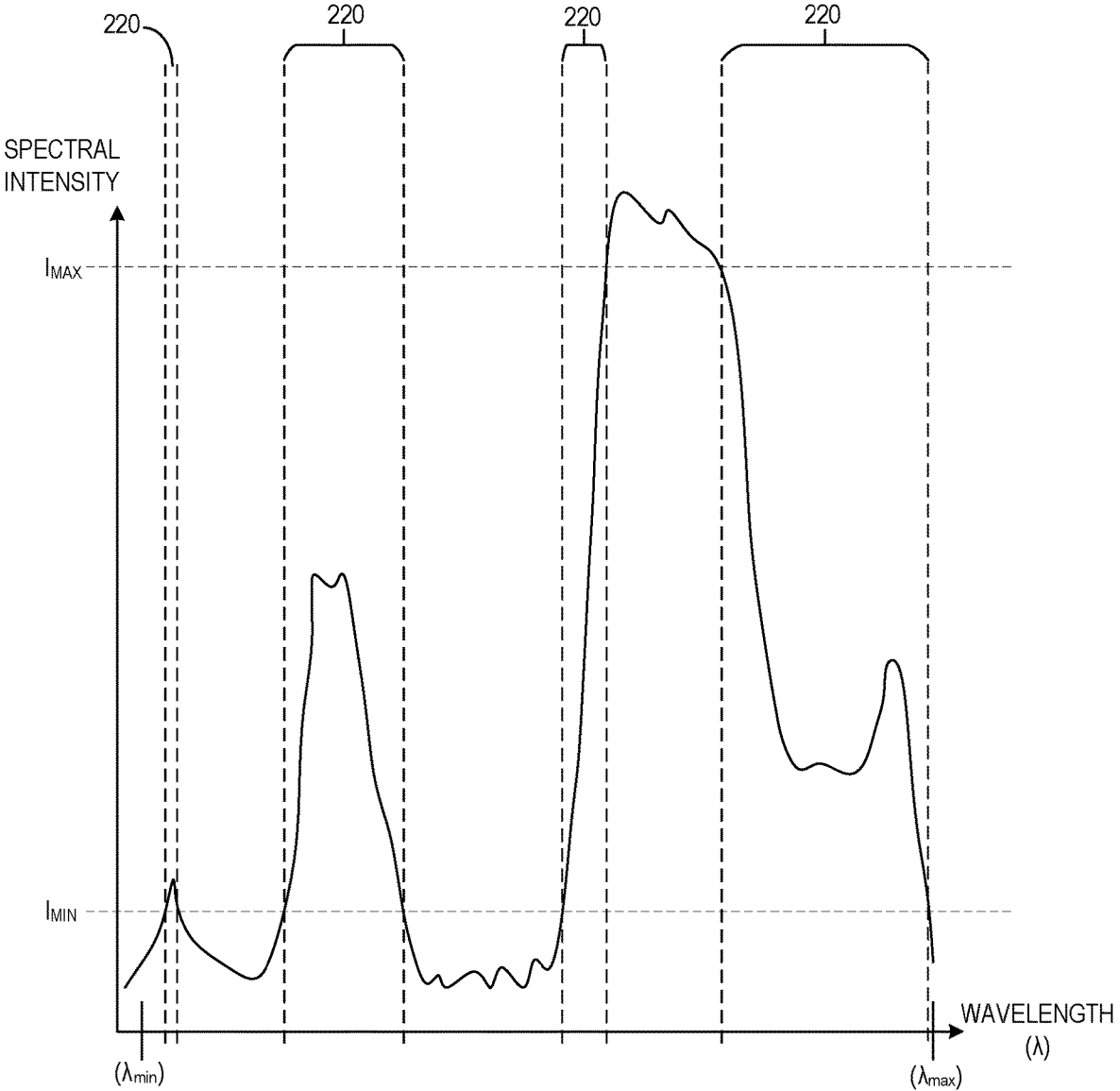
FIG. 2 illustrates generally a spectral plot generated by an optical system of an example composition identification system.

FIG. 2 illustrates generally a spectral plot generated by an optical system of an example composition identification system. The spectral plot can represent light reflected from a reference target, such as a flat white reference target, illuminated by an illumination source of an example composition identification system. The vertical axis provides values of spectral intensity and the horizontal axis provides wavelengths between and near the wavelengths ($\lambda_{min}, \lambda_{max}$) of the illumination source. The spectral plot indicates that the optical system has not been configured with one or more of the optics of the example composition identification system or with the illumination source of the example composition identification system. For example, intensity saturations of certain wavelengths above a first threshold ($I_{MAX}$) and very low intensities of certain wavelengths below a second threshold ($I_{MIN}$) provide the indications that the optical system has not been optimally configured. Furthermore, the wavelengths associated with saturation and very low intensity, unless compensated for, are generally of little value in helping identify composition of a target. As such, the uncompensated spectral information 220 allows just a few bands of wavelength information for use in identifying composition of a target. Since the target used to generate the spectral plot of FIG. 2 is a flat, white reference, it is anticipated that the useable bands of spectrum will be reduced upon trying to identify an anatomical target, as the target will most likely not be flat nor the same shade of white as the reference target and can scatter and absorb certain wavelengths, reducing the intensity of the reflected illumination of those wavelengths.

Figure 3:
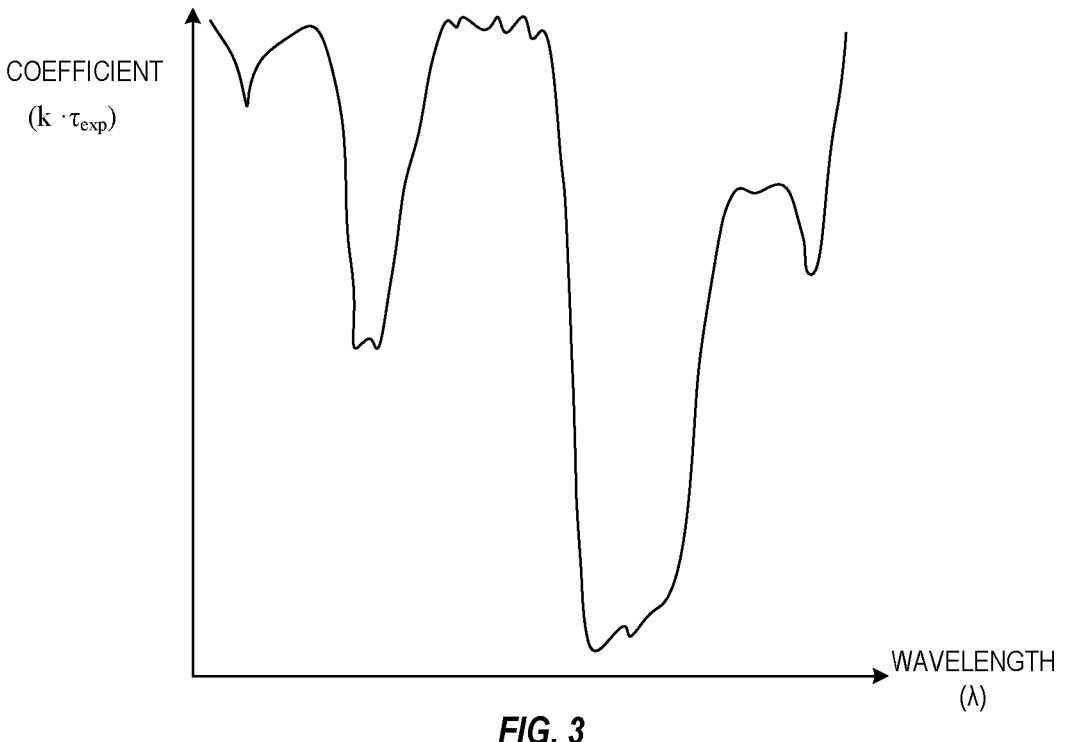
FIG. 3 illustrates graphically programming parameters for an example optical sensor system of a composition identification system to permit collection and analysis of reflected light over a wide range of wavelengths.

FIG. 3 illustrates graphically programming parameters for an example optical sensor system of a composition identification system to permit collection and analysis of reflected light over a wide range of wavelengths. The vertical axis is a coefficient value representative of a product of gain (k) and exposure duration ($\tau_{exp}$). The horizontal axis is wavelength ($\lambda$). The coefficient value ($k*\tau_{exp}$) for each wavelength is designed to adjust gain (k) or exposure duration ($\tau_{exp}$) of certain elements of the optical sensor such that the spectral information provided by the system in response to a reference target are normalized. During calibration, uncompensated intensities of wavelengths that saturate the optical sensor can be compensated by reducing the gain (k) of that wavelength and/or reducing the exposure duration ($\tau_{exp}$). Also during calibration, uncompensated intensities of wavelengths that are below a minimum threshold ($I_{MIN}$) of the optical sensor can be compensated by increasing the gain (k) of that wavelength and/or increasing the exposure duration ($\tau_{exp}$). In the illustrated example, coefficient values ($k*\tau_{exp}$) represented graphically are designed to provide a flattened spectral response of the system of FIG. 2 when the system illuminates and captures light reflected from the flat white reference target. The flattened response can be targeted such that each wavelength intensity across the range of wavelengths remains within a narrow range of useful intensities, for example, between $I_{MAX}$ and $I_{MIN}$. In certain examples, the flattened response can be targeted such that each wavelength intensity across the range of wavelengths remains within a narrow range of intensities centered about a midway point between the maximum useful intensity (e.g., $I_{MAX}$) of the optical sensor and the minimum useful intensity (e.g., $I_{MIN}$) of the optical sensor. In certain examples, the narrow range of intensities can represent less than 50 percent of the useful range of the optical sensor, less than 40 percent of the useful range of the optical sensor, less than 30 percent of the useful range of the optical sensor, less than 20 percent of the useful range of the optical sensor, less than 10 percent of the useful range of the optical sensor, less than 5 percent of the useful range of the optical sensor, less than 2 percent of the useful range of the optical sensor, or less than 1 percent of the useful range of the optical sensor.

Figure 4:
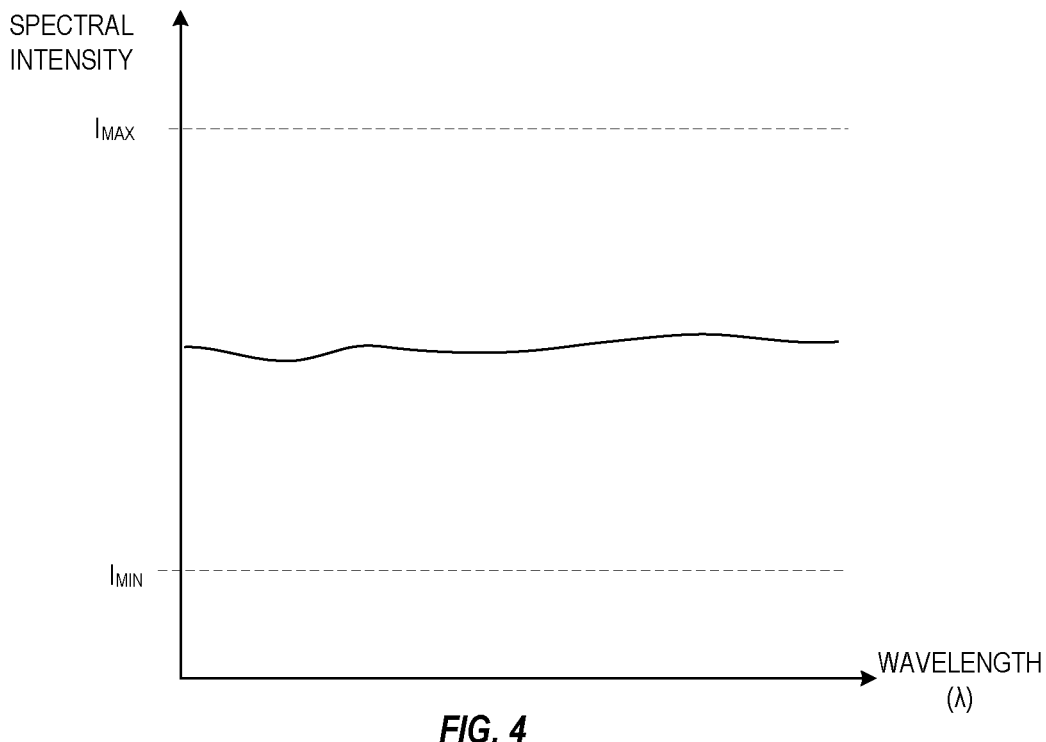
FIG. 4 illustrates generally an example plot of spectral information of a flat white reference target generated from an optical system configured according to the present subject matter.

In certain examples, modification of the gain and exposure duration can be determined to be calibrated when the spectral intensity of the light reflected from the white reference target is about half the upper threshold intensity (e.g., $I_{max}/2$). FIG. 4 illustrates generally an example plot of spectral information of a flat white reference target generated from an optical system configured according to the present subject matter. The vertical axis provides values of signal strength and the horizontal axis provides wavelengths of or near the wavelengths of the illumination source.

After the system is adjusted and can provide a relatively flat spectral response across a range of wavelengths of light reflected from a reference target that is highly reflective and substantially lossless (e.g. a flat, white, reference target), the system can allow that full spectrum to be used to identify composition characteristics of anatomical targets encountered during, for example, endoscopic or laparoscopic procedures. The ability of using the full spectrum of the illumination source light can allow for more accurate identification of composition than using only portions of the illumination light spectrum as is done using conventional methods.

FIG. 5 illustrates generally an example method for calibrating a composition identification system according to the present subject matter. At 501, an optical sensor of the composition identification system can receive light from a reference target, such as reflected light from a flat, white, reference target. A 503, a controller of the composition identification system can determine a first spectral response of the light across a range of wavelengths based on a signal from the optical sensor. At 505, the controller can determine whether a first spectral intensity corresponding to a first wavelength of the spectral response is below a first threshold. At 507, the controller can increase an exposure duration of the optical sensor for the first wavelength in response to determining the first spectral intensity corresponding to the first wavelength of the spectral response is below the first threshold. Increasing the exposure can provide more spectral intensity for the corresponding wavelength of light and can add additional information for assisting in identifying the composition of an actual target.

In some examples, the controller can increase a gain of the optical sensor for the first wavelength in response to determining the first spectral intensity corresponding to the first wavelength of the spectral response is below the first threshold. In some examples, the controller can increase an exposure duration and a gain of the optical sensor for the first wavelength in response to determining the first spectral intensity corresponding to the first wavelength of the spectral response is below the first threshold. In some examples, if the light from the illumination source at a wavelength is too dim, or the optics significantly absorb energy at that wavelength, the controller can ignore that wavelength.

In certain examples, if the controller determines a second spectral intensity corresponding to a second wavelength of the spectral response is above a second threshold, the controller can decrease a gain of the optical sensor for the second wavelength. Decreasing the gain can lower the spectral intensity for the corresponding wavelength of light such that the optical sensor is not saturated and can add additional information for assisting in identifying the composition of an actual target. In certain examples, if the controller determines a second spectral intensity corresponding to a second wavelength of the spectral response is above a second threshold, the controller can decrease an exposure duration of the optical sensor for the second wavelength. In certain examples, if the controller determines a second spectral intensity corresponding to a second wavelength of the spectral response is above a second threshold, the controller can decrease a gain and exposure duration of the optical sensor for the second wavelength.

A complete calibration can include repeating the procedure described above for multiple wavelengths throughout the range of wavelengths. Upon calibrating the full spectrum of wavelengths available via the optical sensor, the composition identification system can be used generate spectral information of light reflected from an anatomical target, and can use the spectral intensity information generated with the compensated gains and exposure durations to identify the composition of the anatomical target. In some examples, the spectral information of the anatomical target generated with the calibrated controller and optical sensor can be compared by the controller to spectral information of known substances to identify the composition of the anatomical target. Because the spectral information is based on a baseline configuration that minimizes spectral effects of the illumination source and the optics, the library of spectral information for known substances can be significantly reduced. Also, the fewer library comparisons can result in more timely composition identification.

Accordingly, for any particular wavelength being calibrated for the optical system, the exposure time and/or gain of the optical sensor system (e.g. spectrometer) may be increased to account for optical distortion in the optical system that results in a spectral intensity that is below a desired level. Also, for any particular wavelength being calibrated for the optical system, the exposure time and/or gain of the optical sensor system may be decreased to account for optical distortion in the optical system that results in a spectral intensity that is above a desired level. In this manner, either or both of the optical sensor system's exposure time and gain during calibration (e.g. with the incident light being onto a reflective and largely lossless calibration target) can be upwardly adjusted to compensate for low intensity optical signals at particular wavelengths, and downwardly adjusted to compensate for high intensity optical signals at particular wavelengths, to ultimately calibrate the optical sensor system (e.g. spectrometer). These upward or downward gain and/or exposure adjustments across a range of light source wavelengths enable post-calibration optical signals to be recognized at the spectrometer or other optical sensor system without significant distortion that would otherwise adversely affect the accuracy of those post-calibration signals.

In some examples, the composition identification system described herein can include a light source, optical components, a ureteroscope or other endoscope, a reflective calibration target, and a spectrometer that can operate with the controller. A spectrometer of the composition identification system can be adjusted. After the spectrometer has been adjusted, calibrating the composition identification system can create a mostly flattened waveform. After the composition identification system has been calibrated, a second state that looks the same structurally, but with renal calculi (or other anatomical target) used during normal medical lithotripsy can then show an example of the spectral analysis positioned over the calibrated/flattened curve to depict that during the procedure the composition identification system can produce a clear image of the reflected light, because the spectrometer has been adjusted according to distortion by the same light source, the same optical components, the same fiber through the endoscope, and so forth. In other words, the system can occupy a first state, in which the system and/or system operator can adjust the gain and exposure on the spectrometer to account for all light sources, all optical components, and scope fiber distortion. The system can then occupy a second state, in which the medical procedure is actually occurring. In the second state, the resulting spectral response can be clearly seen (and the stone/tissue more accurately identified) because of the adjustment or adjustments made in the first state.

Notes and Examples

Example 1 is a method for calibrating a composition identification system, the method comprising: receiving light at an optical sensor from a reference target; determining a first spectral response of the light across a range of wavelengths; determining whether a first spectral intensity corresponding to a first wavelength of the first spectral response is below a first threshold; and increasing an exposure duration of the optical sensor for the first wavelength in response to determining the first spectral intensity corresponding to the first wavelength of the first spectral response is below the first threshold to provide a calibrated first exposure duration.

Example 2 is the method of Example 1, optionally further including increasing a gain of the optical sensor for the first wavelength in response to determining the first spectral intensity corresponding to the first wavelength of the first spectral response is below the first threshold.

Example 3 is the method of any one of Examples 1-2, optionally further including: determining whether a second spectral intensity corresponding to a second wavelength of the first spectral response is above a second threshold; and decreasing a gain of the optical sensor for the second wavelength in response to determining the second spectral intensity corresponding to the second wavelength of the first spectral response is above the second threshold.

Example 4 is the method of any one of Examples 1-2, optionally further including: decreasing an exposure duration of the optical sensor for the second wavelength in response to determining the second spectral intensity corresponding to the second wavelength of the first spectral response is above the second threshold.

Example 5 is the method of any one of Examples 1-4, optionally further configured such that the range of wavelengths includes a visible spectrum of 400 nm to 700 nm in wavelength.

Example 6 is the method of any one of Examples 1-5, optionally further configured such that receiving light at an optical sensor from a reference target includes receiving light reflected from a reference target.

Example 7 is the method of any one of Examples 1-6, optionally further configured such that receiving light at an optical sensor from a reference target includes conveying the light via a medical scope.

Example 8 is the method of any one of Examples 1-7, optionally further including: receiving light at an optical sensor from a second target; determining a second spectral response of the light across a range of wavelengths using the calibrated first exposure duration; and identifying a composition of the second target using the second spectral response.

Example 9 is a composition identification system, comprising: an optical sensor configured to sense light over a range of wavelengths and to provide spectral information of the light; a controller configured to receive the spectral information from the optical sensor, and, in a calibration mode, to determine whether a first spectral intensity corresponding to a first wavelength of the spectral information is below a first threshold; and to increase an exposure duration of the optical sensor for the first wavelength to provide a first modified exposure duration in response to a determination the first spectral intensity corresponding to the first wavelength of the spectral information is below the first threshold.

Example 10 is the composition identification system of Example 9, optionally configured such that the controller is configured to increase a gain of the optical sensor for the first wavelength in response to a determination the first spectral intensity corresponding to the first wavelength of the spectral information is below the first threshold.

Example 11 is the composition identification system of any one of Examples 9-10, optionally configured such that the controller is configured to: determine whether a second spectral intensity corresponding to a second wavelength of the spectral information is above a second threshold; and decrease a gain of the optical sensor for the second wavelength in response to a determination the second spectral intensity corresponding to the second wavelength of the spectral information above the second threshold.

Example 12 is the composition identification system of any one of Examples 9-11, optionally configured such that the controller is configured to decrease an exposure duration of the optical sensor for the second wavelength in response to a determination the second spectral intensity corresponding to the second wavelength of the spectral information above the second threshold.

Example 13 is the composition identification system of any one of Examples 9-12, optionally configured such that the range of wavelengths includes a visible spectrum of 400 nm to 700 nm in wavelength.

Example 14 is the composition identification system of any one of Examples 9-13, optionally further including a medical scope configured to convey the light to the optical sensor.

Example 15 is the composition identification system of any one of Examples 9-14, optionally configured such that the medical scope is an endoscope.

Example 16 is the composition identification system of any one of Examples 9-15, optionally configured such that the medical scope is an ureteroscope.

Example 17 is the composition identification system of any one of Examples 9-16, optionally configured such that the optical sensor is configured to receive light from a second target; and wherein the controller is configured to: determine a second spectral response of the light across a range of wavelengths using the first modified exposure duration; and identify a composition of the second target using the second spectral response.

Example 18 is at least one non-transitory machine-readable medium including instructions that, when executed by processing circuitry, cause the processing circuitry to perform operations, the operations comprising: sensing light at an optical sensor from a reference target; determining a first spectral response of the light across a range of wavelengths; determining whether a first spectral intensity corresponding to a first wavelength of the first spectral response is below a first threshold; and increasing an exposure duration of the optical sensor for the first wavelength to provide a first modified exposure duration in response to determining the first spectral intensity corresponding to the first wavelength of the first spectral response is below the first threshold a calibrated first exposure duration.

Example 19 is the at least one non-transitory machine-readable medium of Example 18, optionally further configured such that the operations further include increasing a gain of the optical sensor for the first wavelength in response to determining the first spectral intensity corresponding to the first wavelength of the spectral response is below the first threshold.

Example 20 is the at least one non-transitory machine-readable medium of any one of Examples 18-19, optionally further configured such that the operations further include: determining whether a second spectral intensity corresponding to a second wavelength of the first spectral response is above a second threshold; and decreasing a gain of the optical sensor for the second wavelength in response to determining the second spectral intensity corresponding to the second wavelength of the first spectral response is above the second threshold.

Example 21 is the at least one non-transitory machine-readable medium of any one of Examples 18-20, optionally further configured such that the operations further include decreasing an exposure duration of the optical sensor for the second wavelength in response to determining the second spectral intensity corresponding to the second wavelength of the spectral response is above the second threshold.

Example 22 is the at least one non-transitory machine-readable medium of any one of Examples 18-21, optionally further configured such that the operations further include: receiving light at an optical sensor from a second target; determining a second spectral response of the light across a range of wavelengths using the first modified exposure duration; and identifying a composition of the second target using the second spectral response.

Example 23 is a method of operating a composition identification system, the method comprising: illuminating a reference target with light from an illumination source, the light having a range of wavelengths spanning a majority of a visible spectrum; receiving light reflected from the reference target at an optical sensor of the composition identification system; adjusting multiple gains and exposure durations of the optical sensor to provide a flattened, reference, spectral response about a target spectral intensity for the range of wavelengths to provide a calibrated optical sensor; illuminating a first target with the light from the illumination source; receiving light reflected from the first target at the calibrated optical sensor; providing a first spectral intensity curve representative of a composition of the first target; and comparing the first spectral intensity curve to one or more reference spectral intensity curves to identify the composition of the first target.

Example 24 is an apparatus, comprising: an optical sensor configured to generate a first signal representative of a reference target and a second signal representative of a reference material; and a controller configured to: receive the first signal; adjust gains and exposures of the optical sensor across a range of wavelengths based on the first signal to provide first adjusted gains and exposures and to flatten a spectral response of the first signal; receive the second signal; and further adjust the gains and exposures of the optical sensor to provide second adjusted gains and exposures and to match a frequency response of the second signal to a model frequency response for the reference material.

Example 25 is the apparatus of Example 24, optionally further configured such that the optical sensor is configured to generate a third signal representative of a second material using the second adjusted gains and exposures; and wherein the controller is configured to receive the third signal and to identify at least a portion of the second material based on a frequency response of the third signal.

Example 26 is the apparatus of any one of Examples 24-25, optionally further including an illumination source configured to illuminate the reference target and the reference material.

Example 27 is the apparatus of any one of Examples 24-26, optionally further configured such that the illumination source is a wide-spectrum illumination source configured to provide light having wavelengths between 400 nm and 700 nm.

Example 28 is the apparatus of any one of Examples 24-27, optionally further including first optics configured to guide light of the illumination source to the reference target and to the reference material.

Example 29 is the apparatus of any one of Examples 24-28, optionally further including second optics configured to guide reflected light from the reference target and the reference material to the optical sensor.

Example 30 is at least one machine-readable medium including instructions that, when executed by processing circuitry, cause the processing circuitry to perform operations to implement of any of Examples 1-29.

Example 31 is an apparatus comprising means to implement of any of Examples 1-29.

Example 32 is a system to implement of any of Examples 1-29.

Example 33 is a method to implement of any of Examples 1-29.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, the terms "including" and "comprising" are open-ended, that is, a system, device, article, composition, formulation, or process that includes elements in addition to those listed after such a term are still deemed to fall within the scope of subject matter discussed. Moreover, such as may appear in a claim, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of a claim. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. The following aspects are hereby incorporated into the Detailed Description as examples or embodiments, with each aspect standing on its own as a separate embodiment, and it is contemplated that such embodiments can be combined with each other in various combinations or permutations.

What is claimed is:

1. A method for calibrating a composition identification system, the method comprising:
   receiving light at an optical sensor from a substantially losslessly reflective reference target;
   determining a first spectral response of the light across a range of wavelengths;
   determining whether a first spectral intensity corresponding to a first wavelength of the first spectral response is below a first threshold;
   increasing both an exposure duration and a gain of the optical sensor for the first wavelength in response to determining the first spectral intensity corresponding to the first wavelength of the first spectral response is below the first threshold to provide a calibrated first exposure duration;
   determining whether a second spectral intensity corresponding to a second wavelength of the first spectral response is above a second threshold; and
   decreasing a gain of the optical sensor for the second wavelength in response to determining the second spectral intensity corresponding to the second wavelength of the first spectral response is above the second threshold.

2. The method of claim 1, further comprising:
   decreasing an exposure duration of the optical sensor for the second wavelength in response to determining the second spectral intensity corresponding to the second wavelength of the first spectral response is above the second threshold.

3. The method of claim 1, wherein the range of wavelengths includes a visible spectrum of 400 nm to 700 nm in wavelength.

4. The method of claim 1, wherein receiving light at an optical sensor from a reference target includes receiving light reflected from a reference target.

5. The method of claim 1, wherein receiving light at an optical sensor from a reference target includes conveying the light via a medical scope.

6. The method of claim 1, further comprising:
   receiving light at an optical sensor from a second target;
   determining a second spectral response of the light across a range of wavelengths using the calibrated first exposure duration; and
   identifying a composition of the second target using the second spectral response.

7. A method for calibrating a composition identification system, the method comprising:
   receiving light at an optical sensor from a substantially losslessly reflective reference target;

determining a first spectral response of the light across a range of wavelengths;
   determining whether a first spectral intensity corresponding to a first wavelength of the first spectral response is below a first threshold;
   increasing an exposure duration of the optical sensor for the first wavelength in response to determining the first spectral intensity corresponding to the first wavelength of the first spectral response is below the first threshold to provide a calibrated first exposure duration;
   determining whether a second spectral intensity corresponding to a second wavelength of the first spectral response is above a second threshold; and
   decreasing a gain of the optical sensor for the second wavelength in response to determining the second spectral intensity corresponding to the second wavelength of the first spectral response is above the second threshold.

8. The method of claim 7, further comprising:
   decreasing an exposure duration of the optical sensor for the second wavelength in response to determining the second spectral intensity corresponding to the second wavelength of the first spectral response is above the second threshold.

9. The method of claim 7, wherein the range of wavelengths includes a visible spectrum of 400 nm to 700 nm in wavelength.

10. The method of claim 7, wherein receiving light at an optical sensor from a reference target includes receiving light reflected from a reference target.

11. The method of claim 7, wherein receiving light at an optical sensor from a reference target includes conveying the light via a medical scope.

12. The method of claim 7, further comprising:
   receiving light at an optical sensor from a second target;
   determining a second spectral response of the light across a range of wavelengths using the calibrated first exposure duration; and
   identifying a composition of the second target using the second spectral response.

13. A method for calibrating a composition identification system, the method comprising:
   receiving light at an optical sensor from a substantially losslessly reflective reference target;
   determining a first spectral response of the light across a range of wavelengths;
   determining whether a first spectral intensity corresponding to a first wavelength of the first spectral response is below a first threshold;
   increasing a gain of the optical sensor for the first wavelength in response to determining the first spectral intensity corresponding to the first wavelength of the first spectral response is below the first threshold to provide a calibrated first exposure duration;
   determining whether a second spectral intensity corresponding to a second wavelength of the first spectral response is above a second threshold; and
   decreasing a gain of the optical sensor for the second wavelength in response to determining the second spectral intensity corresponding to the second wavelength of the first spectral response is above the second threshold.

14. The method of claim 13, further comprising:
   decreasing an exposure duration of the optical sensor for the second wavelength in response to determining the second spectral intensity corresponding to the second wavelength of the first spectral response is above the second threshold.

15. The method of claim 13, wherein the range of wavelengths includes a visible spectrum of 400 nm to 700 nm in wavelength.

16. The method of claim 13, wherein receiving light at an optical sensor from a reference target includes receiving light reflected from a reference target.

17. The method of claim 13, wherein receiving light at an optical sensor from a reference target includes conveying the light via a medical scope.

18. The method of claim 13, further comprising:

receiving light at an optical sensor from a second target;

determining a second spectral response of the light across a range of wavelengths using the calibrated first exposure duration; and identifying a composition of the second target using the second spectral response.

\* \* \* \* \*